(12) United States Patent
Ma et al.

(10) Patent No.: US 7,813,536 B2
(45) Date of Patent: Oct. 12, 2010

(54) IMAGE MEASURING APPARATUS AND METHOD, AND IMAGE MEASURING SYSTEM FOR GLOMERULAR FILTRATION RATE

(75) Inventors: Hongfeng Ma, Shenyang (CN); Qiang Di, Shenyang (CN); Lei Wu, Shenyang (CN); Honglei Fu, Shenyang (CN); Longwei Mei, Shenyang (CN); Liang Tian, Shenyang (CN); Songmin Quan, Shenyang (CN); Jun Zhang, Shenyang (CN); Yan Kang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 974 days.

(21) Appl. No.: 11/636,475

(22) Filed: Dec. 11, 2006

(65) Prior Publication Data

US 2008/0025589 A1    Jan. 31, 2008

(30) Foreign Application Priority Data

Jul. 27, 2006    (CN) .................... 2006 1 0103738

(51) Int. Cl.
G06K 9/00    (2006.01)

(52) U.S. Cl. ..................... 382/128; 382/130

(58) Field of Classification Search ................ 382/128, 382/131, 181; 600/410
See application file for complete search history.

(56) References Cited

U.S. PATENT DOCUMENTS 5,956,435 A * 9/1999 Buzug et al. ............... 382/283
7,146,204 B2 * 12/2006 Degani et al. .............. 600/410
7,468,513 B2 * 12/2008 Charron et al. .......... 250/363.05
2005/0090736 A1 * 4/2005 Sommer ..................... 600/425

FOREIGN PATENT DOCUMENTS

CN    1449721    4/2002

OTHER PUBLICATIONS

Yuefeng Xu et al., "Research Progress in Imaging Technique on Renal Function", Chinese Journal of Radiology, Aug. 2004, vol. 38, No. 8, pp. 885-889.

* cited by examiner

Primary Examiner—Tom Y Lu
(74) Attorney, Agent, or Firm—Stephen A. Bent; Foley & Lardner LLP

(57) ABSTRACT

The present invention discloses an abdominal CT image measuring apparatus and method. The abdominal CT image measuring apparatus includes: an interface unit; a part recognizing unit and a characteristic data computing unit. The present invention can determine the specific region of the part under test with a little amount of computation, by registration and subtraction operation on the two-phase scan images. This is easy to be carried out in computers, thus the computing speed of the characteristic data can be guaranteed and the efficiency can be improved. By the recognizing of the kidney regions and the abdominal aorta region in the present invention, the glomerular filtration rates obtained by applying the key concept of the present invention to the image measuring of glomerular filtration rate can meet the clinical application requirements in both precision and speed.

18 Claims, 4 Drawing Sheets

IMAGE MEASURING APPARATUS AND METHOD, AND IMAGE MEASURING SYSTEM FOR GLOMERULAR FILTRATION RATE

FIELD OF THE INVENTION

The present invention relates to the field of image processing, and more particularly, to a method and an apparatus for measuring diagnostic reference values based on abdominal CT images, and an image measuring system for glomerular filtration rate.

BACKGROUND OF THE INVENTION

Computer Tomography (CT) uses computer-controlled X-rays to scan human in stratum. It can accurately display an anatomical structure by comparing the different densities of human body tissues presented under X-rays. Medical images obtained by CT are usually inspected and measured by physicians or the like to obtain required characteristic data as diagnostic basis. However, the measuring method for diagnostic reference values of CT images in the prior art depends more on manual work, resulting in a low efficiency and an insufficient precision.

For example, Chinese patent application No. 03136006.8 discloses a medical image processing apparatus for processing medical image(s) generated by a medical image device, and the medical image processing apparatus includes: an interface, configured to obtain medical image(s); a processor, configured to determine a smooth line along an arched portion of a sample in the medical image(s) obtained by the interface; and a computing apparatus, configured to compute the camber of the arched portion based on the smooth line determined by the processor. Some characteristic data, such as the camber of the arched portion, can be obtained by use of the above image measuring method.

However, to obtain some preciser and complexer characteristic data, it is needed to collect the basic characteristic data such as CT value and volume precisely and quickly and to have a large amount of complex computation. At this point, the existing measuring method becomes insufficient.

For example, for determining the characteristic data of a part with a complicated shape, such as the accurate volume of the part, the following measuring method is usually employed in the prior art: a few scattered edge points in the critical area of the part under test are collected to determine an approximate contour, and then the volume of the part under test is determined based on the empirical volume value of the part. This method often creates a big error. In another method, a region is approximately determined by an operator according to the obtained images, for example, the region is marked on each single-slice CT image by a curve, then the region is measured in various ways, thus the volume of the part under test is obtained. Although the volume of the part under test can be obtained by the above methods, due to the complex shape of the part under test on the medical image, it is difficult to obtain an accurate value and sufficient parameters. As a result, the characteristic data obtained such as volume have a low precision and cannot be applied to cases with high precision requirement. Moreover, because the above methods depend more on personal experience and manual operations, the efficiency is usually very low.

As another example, it is required to obtain the average value of a certain characteristic data of a part under test. The following method is usually employed in the prior art: the part under test is scaned by CT to obtain tomographic images of an appropriate position thereof; some discrete points at the position of the part under test on the images are selected, and the average value of the characteristic data of these discrete points is computed so as to approximately obtain the average value of the certain characteristic data of the part under test. However, due to the fact that the distribution of the characteristic data in the part under test is not always uniform, the precision of the average value of the characteristic data obtained by the above method is usually low. In order to improve the precision, the operator need to determine and collect lots of representative points to obtain a more accurate result, at the cost of much more time and cost and a lower efficiency.

Consequently, by use of the prior art image measuring methods, the resulting precision of the characteristic data of the part under test is relatively insufficient, or the speed and efficiency of the measuring process are very low (that is, considerable time and cost must be taken to improve the precision).

SUMMARY OF THE INVENTION

The present invention aims to provide an abdominal CT image measuring apparatus and method, which can improve the efficiency and precision of the measuring of characteristic data of a part under test, especially at the precondition of meeting the desired efficiency, obtain characteristic data such as CT value, volume, etc. at high precision by image measuring approaches.

The present invention also aims to provide an image measuring system for glomerular filtration rate, which can obtain the characteristic data of kidney, glomerular filtration rate, at high efficiency and high precision, so as to insure the realization and application of the method in clinical use.

The present invention provides an abdominal CT image measuring apparatus, including:

an interface unit, for obtaining two-phase or multi-phase scan images of a part under test, wherein the scan images include plain scan image series and enhanced scan image series;

a part recognizing unit, for recognizing points representing the part under test on the scan images; and a characteristic data computing unit, for extracting CT values of the points representing the part under test, and computing required characteristic data of the part under test based on the difference between the CT values of the points representing a same position of the part under test on the images in different phases.

Preferably, the part recognizing unit includes:

a registering subunit, for outputting the correspondence between the scan images in two different phases by a registration algorithm;

a judging subunit, for comparing the CT values of the corresponding points on the scan images in two different phases;

a part region determining subunit, for determining that the corresponding points on the scan images in two different phases belong to the part under test when the difference between the CT values of the points is greater than or equal to a predetermined threshold.

Preferably, the part recognizing unit recognizes the points representing the part under test on the scan images by at least one of digital subtraction, region growing method, watershed algorithm and ASM algorithm. Preferably, the points belonging to the part under test together constitute the part under test and are displayed on the abdominal CT images.

Preferably, in the abdominal CT image measuring apparatus of the present invention, the interface unit is used for obtaining abdominal CT plain scan images, arterial phase images and delayed phase images; the part recognizing unit is used for recognizing points representing kidneys and abdominal aorta in the plain scan images, the arterial phase images and the delayed phase images, and for segmenting a kidney region and an abdominal aorta region.

The characteristic data computing unit includes:

a kidney volume determining subunit, for extracting the volume and the number of data voxels contained in each of the segmented kidney regions and computing each kidney volume;

an added average CT value determining subunit, for extracting the CT values corresponding to the points in the segmented kidney regions, computing the added average CT values of the kidney regions in the arterial phase and the delayed phase relative to the plain scan images, extracting the CT values corresponding to the points in the segmented abdominal aorta region, and computing the added average CT values of the abdominal aorta region in the arterial phase and the delayed phase relative to the plain scan images;

a curve determining subunit, for obtaining a curve of the average CT value of the abdominal aorta region varying with time by a regression analysis;

a glomerular filtration rate determining subunit, for computing the glomerular filtration rates based on the above parameters.

The part recognizing unit includes:

a selecting subunit, for selecting a point at the abdominal aorta on the plain scan images as a seed point;

a growing subunit, for starting a region growing from the seed point and obtaining a region of which the CT value is greater than a preset growth threshold, wherein the region is the segmented abdominal aorta on the plain scan images;

an abdominal aorta region determining subunit, for obtaining, on the arterial phase images and the delayed phase images, a region corresponding to the segmented abdominal aorta on the plain scan images, based on the segmented abdominal aorta on the plain scan images and the correspondence between the plain scan images and the arterial phase images as well as the correspondence between the plain scan images and the delayed phase images output by the registration algorithm.

Preferably, the characteristic data computing unit further includes a correcting subunit for correcting the computed glomerular filtration rates. The part recognizing unit further includes a right and left kidney distinguishing subunit for determining the right and left kidneys in the kidney regions. The glomerular filtration rate determining subunit is used for computing the glomerular filtration rates of the right and left kidneys respectively.

The present invention further provides a method for measuring abdominal CT images, including:

an obtaining step, for obtaining two-phase or multi-phase scan images of a part under test, wherein the scan images include plain scan image series and enhanced scan image series;

a recognizing step, for recognizing points representing the part under test on the scan images; and a computing step, for extracting the CT values of the points representing the part under test, and computing required characteristic data of the part under test based on the difference between the CT values of the points representing a same position of the part under test on the images in different phases.

Preferably, the points representing the part under test on the scan images are recognized by the following steps: outputting the correspondence between the scan images in two different phases by a registration algorithm; comparing the CT values of the corresponding points on the scan images in two different phases; and determining that the corresponding points on the scan images in two different phases belongs to the part under test when the difference between the CT values of the points is greater than or equal to a predetermined threshold. Or, the points representing the part under test on the scan images are recognized at least one of digital subtraction method, region growing method, watershed algorithm or ASM algorithm. Preferably, the points belonging to the part under test together constitute the part under test and are displayed on the abdominal CT images.

Preferably, in the method for measuring abdominal CT images according to the present invention, the scan images include abdominal CT plain scan images, arterial phase images and delayed phase images; points representing kidneys and abdominal aorta on the plain scan images, the arterial phase images and the delayed phase images are recognized, and the kidney regions and the abdominal aorta region are segmented.

The computing step includes:

extracting the volume and the number of data voxels contained in each of the segmented kidney regions, and computing each kidney volume;

extracting the CT values corresponding to the points in the segmented kidney regions, and computing the added average CT values of the kidney regions in the arterial phase and delayed phase relative to the plain scan images;

extracting the CT values corresponding to the points in the segmented abdominal aorta region, and computing the added average CT values of the abdominal aorta region in the arterial phase and the delayed phase relative to the plain scan images;

obtaining a curve of the average CT value of the abdominal aorta region varying with time by a regression analysis; and computing the glomerular filtration rate based on the above parameters.

Preferably, the abdominal aorta is segmented on the plain scan images by the following steps:

selecting a point at the abdominal aorta on the plain scan images as a seed point; and starting a region growing from the seed point and obtaining a region of which the CT value is greater than the preset growth threshold, wherein the region is the segmented abdominal aortaon the plain scan images. Preferably, the abdominal aorta is segmented from the arterial phase images and the delayed phase images by the following step: obtaining, on the arterial phase images and the delayed phase images, a region corresponding to the abdominal aorta segmented on the plain scan images, based on the segmented abdominal aorta on the plain scan images and the correspondence between the plain scan images and the arterial phase images as well as the correspondence between the plain scan images and the delayed phase images output by the registration algorithm.

Preferably, the method for measuring abdominal CT images further includes correcting the computed glomerular filtration rates. The recognizing step further includes determining the right and left kidneys in the kidney regions. The computing step further includes computing the glomerular filtration rates of the right and left kidneys respectively.

The present invention further provides an image measuring system for glomerular filtration rate, including an image scanning and reconstructing subsystem, an image-processing subsystem, wherein:

the image scanning and reconstructing subsystem is used for scanning and outputting plain scan images, arterial phase images and delayed phase images; and the image-processing subsystem is used for image processing and characteristic data measuring, and includes:

a segmenting unit, for segmenting kidneys and abdominal aorta from the plain scan images, the arterial phase images and the delayed phase images respectively;

a parameter determining unit, for obtaining the volume and the number of data voxels contained in each kidney region and computing each kidney volume, obtaining the average CT values of the kidney regions and the abdominal aorta region, computing the added average CT values of the kidneys and the abdominal aorta in the arterial phase and the delayed phase, and obtaining a curve of the average CT value of the abdominal aorta varying with time by a regression analysis;

a glomerular filtration rate determining unit, for computing the glomerular filtration rate based on the above parameters; and a display unit, for displaying the glomerular filtration rates.

The information displayed on the display unit further includes: the segmented kidney regions and abdominal aorta region, or the curve of the average CT value of the abdominal aorta varying with time.

In comparison with the prior art, the present invention has the following advantages.

The present invention recognizes all the points representing the part under test on medical images by image processing techniques, and then computes the characteristic data according to the voxel parameters corresponding to the points representing the part under test. Since the part under test may be described accurately by the image points, the precision of the characteristic data can be improved.

Next, the present invention can determine the specific region of the part under test with a little amount of computation, by registration and subtraction operation on the two-phase images. This is easy to be carried out in computers, thus the computing speed of the characteristic data can be guaranteed and the efficiency can be improved. Moreover, it can be guaranteed that the specific regions of the part under test determined on the two images are the same with each other, so errors may be eliminated, and the precision of the characteristic data may be improved especially when dependence between multiple series of data is needed.

Furthermore, when the key concept of the present invention is applied to evaluate glomerular filtration rate, the abdominal aorta is recognized preferably by region growing method due to the uniform distribution of the CT values in the abdominal aorta, then the abdominal aorta on multi-phase images can be obtained easily and rapidly by the computed correspondence between the images. This is especially suitable for the evaluating glomerular filtration rate and can further reduce the amount of computation and improve the efficiency.

The glomerular filtration rate obtained by applying the key concept of the present invention to the evaluating of glomerular filtration rate can meet the clinical application requirements in both precision and speed.

DETAILED DESCRIPTION OF THE EMBODIMENTS

The above objects, characteristics and advantages of the present invention will be further understood by the following detailed description of the present invention in conjunction with the drawings and the preferred embodiments.

Figure 1:
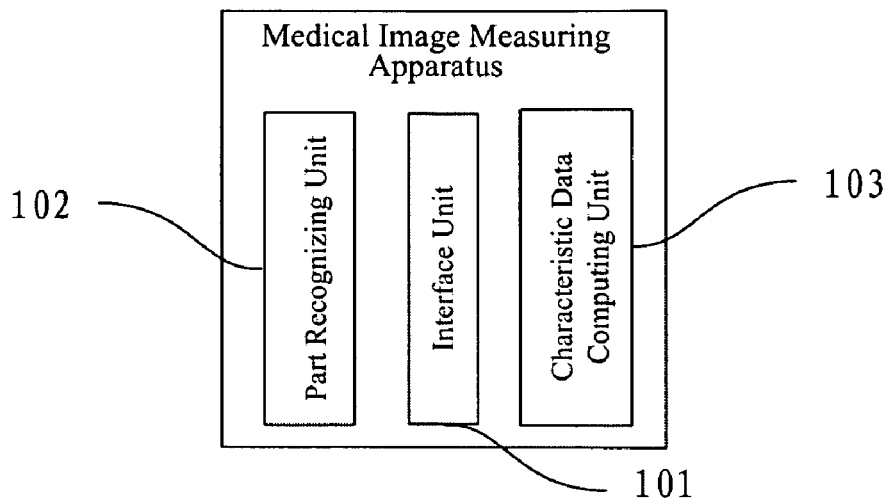
FIG. 1 shows a structure diagram of an abdominal CT image measuring apparatus according to an embodiment of the present invention.

Refer to FIG. 1, which shows a structure diagram of an abdominal CT image measuring apparatus according to an embodiment of the present invention, including:

an interface unit 101, for obtaining two-phase or multi-phase scan images of a part under test, wherein the scanned images include plain scan image series and enhanced scan image series, and the images especially refer to abdominal CT images in the embodiments of the present invention;

a part recognizing unit 102, for recognizing the points representing the part under test on the scan images; and a characteristic data computing unit 103, for extracting the CT values of the points representing the part under test, and computing the required characteristic data of the part under test based on the difference between the CT values of the points representing a same position of the part under test on the images in different phases.

The parts that may be included on the abdominal CT images mainly include kidneys, ureters, urinary bladder, aorta, etc. By recognizing these parts, the computed characteristic data may include renal tubular filtration rate, vessel stenosis and so on.

Plain scan images are obtained by a common CT scan on a part under test. However, some characteristic data cannot be obtained only according to the plain scan images. Thus dynamic data of the part under test may be obtained by adding a contrast medium to the part under test. CT scan images obtained after the addition of the contrast medium to the part under test are referred to as enhanced scan images. The enhanced scan images may relate to a scan or multiple scans.

For example, in the evaluating of glomerular filtration rate, plain scan images may be obtained prior to the addition of the contrast medium to the kidneys, and arterial phase images and delayed phase images may be obtained at different time points after the addition of the contrast medium.

As another example, in the evaluating of glomerular filtration rate, plain scan images may be obtained prior to the addition of the contrast medium to the kidneys, and multiple continuous scans of the same slice are performed at different time points after the addition of the contrast medium, and the multi-phase scan images obtained thereafter are all enhanced scan images (for example, the continuous scans of the same slice are carried out at 0, 15, 20, 32, 37, 42, 59, 64, 69, 86, 91 and 96 s after an intravenous injection of the contrast medium, with a slice thickness of 10 mm).

The single-phase scan may produce a single-slice image, that is, a certain position of the part under test is scanned to obtain single-slice data. The single-phase scan may also produce a series of images, that is, a large portion of the part under test is scanned to obtain the structure data of the range. The structure data is composed of a number of single-slice images. For example, for kidney CT scans, the structure data may be composed of 20 to 30 single-slice images, with a slice thickness of 5 mm.

After the contrast medium is added to the part under test, the CT values of the points representing the part on the enhanced CT images vary with time. Therefore the various required characteristic data may be computed according to the difference between the CT values of the points representing a same position of the part under test on the images in different phases.

A CT value of a CT image reflects the X-ray absorption value (attenuation coefficient u) of a tissue, the unit of which is Hounsfield Unit (Hu). For exemple, the attenuation coefficient of water is taken as a reference, that is, the CT value of water is 0; if the attenuation coefficient of a substance is larger than that of water, it is a positive value; otherwise, the attenuation coefficient of the substance is a negative value. Moreover, the attenuation coefficients of bone cortex and air are taken as an upper limit and a lower limit respectively, which are set as +1000 and −1000 respectively. In general, the processed images are quantified gray level images, and a standard gray level image is a 12-bit gray level image.

The part recognizing unit 102 may process the multi-phase scan abdominal CT images to recognize the points representing the part under test on the scan images in different phases respectively by the following algorithms: digital subtraction method, region growing method, watershed algorithm or ASM algorithm. The part recognizing unit 102 may also display the recognized points on the abdominal CT images in various ways, so that the related persons may learn the part under test visually.

The part recognizing unit 102 according to a preferred embodiment of the present invention may recognize the points representing the part under test on the images by means of image comparison, the advantages of which includes: first of all, the amount of computation is relative small, and thus the points representing the part under test on the multiple images or the multiple series of images may be recognized rapidly; next, the correspondence of the part under test on the multiple images or the multiple series of images can be guaranteed, such that the errors can be reduced. When employing the above method, the part recognizing unit 102 includes the following subunits: a registering subunit, for outputting the correspondence between the scan images in two different phases by a registration algorithm; a judging subunit, for comparing the CT values of the corresponding points on the scan images in two different phases; a part region determining subunit, for determining that the corresponding points on the scan images in two different phases belongs to the part under test when the difference between the CT values of the points is greater than or equal to a predetermined threshold. When the difference between the CT values of the corresponding points is greater than or equal to the predetermined threshold, the part region determining subunit marks each of the points as 1, otherwise as 0. The points marked as 1 constitute the part under test on the images, so as to shown the part under test to the related persons.

On the abdominal CT images, the distribution of the CT values of some parts under test is relatively uniform. If the characteristic data to be computed are CT values only, when to recognize such a part under test, a region may be selected approximately as the part under test manually. Since the distribution of CT values of the part under test is relatively uniform, some selected points may substantially represent the whole part under test, and no precise segmentation is needed.

Besides CT value, the characteristic data computing unit 103 may extract other parameters from the recognized points representing the part under test as required, such as the volume of the data voxels represented by the points and the number of the points for computing the volume of the part under test, the distribution parameters of the points for computing the center of the part under test, and the distribution parameters of the edge points of the part under test for computing the contour curvature of the part under test.

Figure 2:
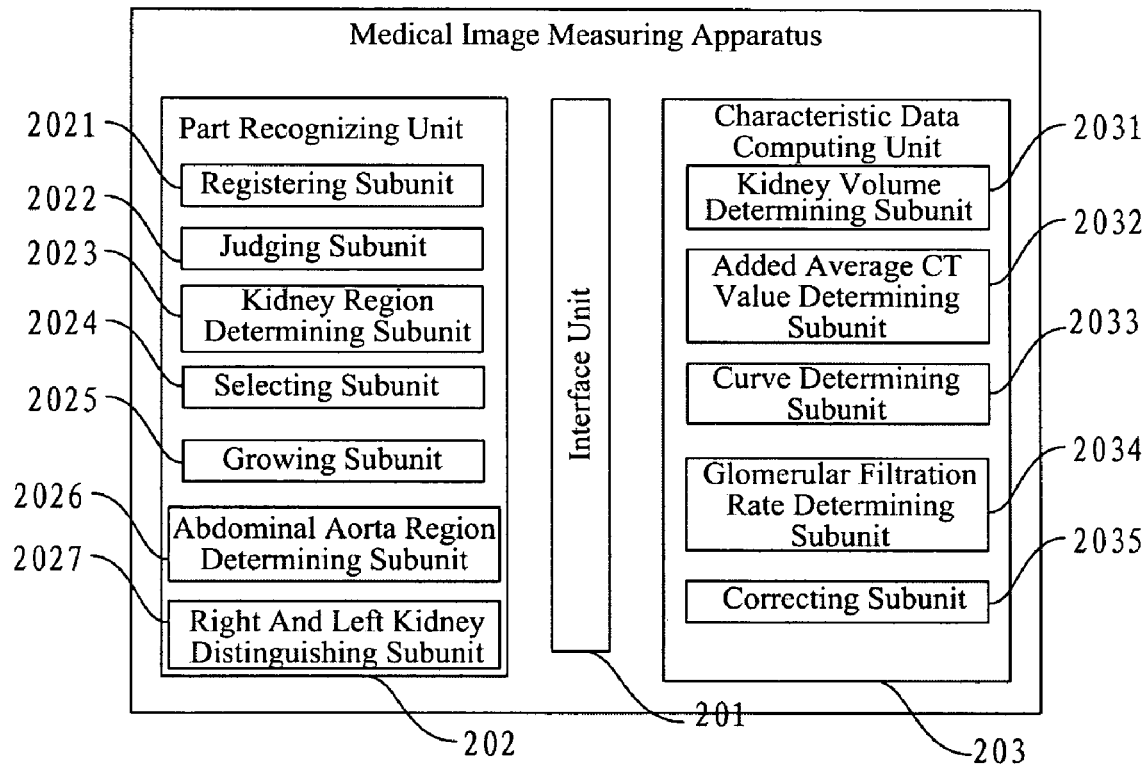
FIG. 2 shows a structure diagram of the apparatus in FIG. 1 according to a preferred embodiment of the present invention.

Referring to FIG. 2, there is shown a structure diagram of the apparatus in FIG. 1 according to an preferred embodiment of the present invention. In the preferred embodiment, the characteristic data of kidney, glomerular filtration rate, is evaluated based on abdominal CT images. The apparatus includes the following units:

an interface unit 201, for obtaining abdominal CT plain scan images, arterial phase images and delayed phase images;

a part recognizing unit 202, for recognizing the points representing the kidneys and the abdominal aorta on the plain scan images, the arterial phase images and the delayed phase images, and for segmenting a kidney region and an abdominal aorta region. Because parameters related to the kidneys and the abdominal aorta are needed in the computation of the glomerular filtration rates, these two parts under test need to be recognized from the CT images;

a characteristic data computing unit 203, for extracting the related parameters from the points representing the kidneys and the abdominal aorta, and for computing the glomerular filtration rates.

Each of the above units will be illustrated in the following description.

The interface unit 201 may obtain the abdominal CT plain scan images, the arterial phase images and the delayed phase images in various ways, such as by connecting with a CT machine directly, by data transmitted from a network, or by means of a mobile storage.

When being used for recognizing kidneys, the part recognizing unit 202 may include the following subunits:

a registering subunit 2021, for outputting the correspondence between the plain scan images and the arterial phase images, as well as the correspondence between the plain scan images and the delayed phase images by a registration algorithm;

a judging subunit 2022, for comparing the CT values of the corresponding points on the scan images in two different phases; and a kidney region determining subunit 2023, for determining the corresponding points on the scan images in any different phases belong to the kidneys when the difference between the CT values of the corresponding points is greater than or equal to a predetermined threshold. When the difference between the CT values of the pair of corresponding points is greater than or equal to a predetermined threshold, the kidney region determining subunit 2023 marks each of the points as 1, otherwise as 0; the points marked as 1 constitute the kidney region on the images.

The registration algorithm employed in the registering subunit 2021 will be briefly introduced as follows.

A registration algorithm usually includes three factors: similarity measure, optimization algorithm and parameter space. Preferably, in the embodiments of the present invention, mutual information value is took as a similarity measure of the registration algorithm, Powell algorithm is employed as the optimization algorithm, and a number of parameters representing the correspondence between two series of images are used to compose the parameter space.

A number of parameters representing the correspondence between two series of images include the translation amounts along the X-, Y- and Z-axes, the angles of rotation around X-, Y- and Z-axes, and scaling factor, etc. For non-rigid registration, the parameters further include distortion factor. Depending on the characteristics of the image to be registered, some or all of the parameters may be selected to constitute the parameter space.

Mutual information is a basic concept in information theory, and is a measure of statistical dependence of two random variables. When two images reach the best registration based on a common anatomical structure, the gray level mutual information of the corresponding pixels thereof should reach the maximum value. Because neither assumption on the relations between the image gray levels under different image modes nor segmentation or pretreatment on the image is needed for the measure, it may be widely applied to the registration of various medical images, and good registration effect can be achieved even if the data of one of the images is partly absent or damaged.

Image registration is essentially the optimization of multiple parameters, that is, searching for the parameter values representing the correspondence between the images wich is reached when the mutual information reaches its maximum value. Therefore, registration essentially is the optimization of registration functions. Preferably, Powell optimization algorithm is employed in the embodiments of the present invention, which optimizes the transformation parameters alternately. Because no gradient is needed to be computed, the speed of searching for maximum mutual information may be increased. As a matter of course, other optimization algorithms such as Brent algorithm can also be employed. For example, Brent algorithm may be used for searching iteratively and estimating registration parameters in each dimension, such that the mutual information increases continuously. Another optimization method, simplex algorithm, may be employed in the embodiments of the present invention. This simplex algorithm does not require any gradient to be computed either. In contrast to the Powell algorithm that only takes a single variable into account, the simplex algorithm takes all variables into account at the same time. However the convergence rate of this method is uncertain. Of course, a combination of the above optimization algorithms may be employed in the embodiments of the present invention to achieve the best effect.

The registration algorithms may insure that the specific region of the part under test determined on the two series of images are the same with each other, so errors may be avoided, and the precision of the characteristic data may be improved especially when a correlation between multiple series of data is needed.

After the registration is completed, the corresponding points of two series of data are obtained based on the registration result (correspondence), and all the corresponding points on the two or two series of images may be compared successively. If the difference between the CT values of the corresponding points is greater than or equal to a predetermined threshold, the part region determining subunit marks each of the points as 1; otherwise as 0. All the points marked as 1 constitute the segmented region of the part under test on the images. Preferably, the points marked as 1 may be shown in different colors or gray levels on the images for easy recognition. As a matter of course, in the embodiments of the present invention, it is not necessary to define how the recognized points may be marked in a computer.

When used for recognizing abdominal aorta, the part recognizing unit 202 may further includes the following subunits:

a selecting subunit 2024, for selecting a point at the abdominal aorta on the plain scan images as a seed point;

a growing subunit 2025, for starting a region growing from the seed point and obtaining a region of which the CT value is greater than a preset growth threshold, wherein the region is the segmented abdominal aorta on the plain scan images; and an abdominal aorta region determining subunit 2026, for obtaining, on the arterial phase images and the delayed phase images, a region corresponding to the segmented abdominal aorta on the plain scan images, based on the segmented abdominal aorta on the plain scan images and the correspondence between the plain scan images and the arterial phase images as well as the correspondence between the plain scan images and the delayed phase images output by a registration algorithm.

The output of the correspondence between the plain scan images and the arterial phase images as well as the correspondence between the plain scan images and the delayed phase images by the registration algorithm may be implemented in the registering subunit 2021. Of course, the abdominal aorta region determining subunit 2026 may also be omitted, and the abdominal aorta regions may be recognized on the arterial phase images and the delayed phase images respectively by succesively carrying out region growings on each of the images by the selecting subunit 2024 and the growing subunit 2025.

The part recognizing unit 202 may also recognize abdominal aorta in other ways, and therefore may include others subunits, which will not be further discussed in detail due to its boundlessness. For example, a region may be selected manually approximately as the recognized abdominal aorta region.

The characteristic data computing unit 203 may include the following subunits.

A kidney volume determining subunit 2031 is provided to extract the volume and the number of the data voxels contained in each of the segmented kidney regions, and for computing each kidney volume.

For the points representing each kidney have been recognized by the part recognizing unit 202, these points constitute each whole kidney. The kidney volume determining subunit 2031 extracts the volume of the data voxels corresponding to the points and counts the points representing each kidney, so as to compute the volume of each kidney.

Since in the embodiments of the present invention the computation is carried out based on all the points representing the part under test on the images, in addition to the volume characteristic data, various other characteristic data may be computed according to various parameters corresponding to the points. It is noted that the "all" defined in item "all of the points" is for illustrative purpose only, because during the recognizing, it is preferred to omit any point mismatching the preset conditions so as to obtain the points representing the part under test on the images.

An added average CT value determining subunit 2032 is provided to extract the CT values corresponding to the points in each of the segmented kidney regions, and computing the added average CT values of the kidney regions in the arterial phase and the delayed phase relative to the plain scan images; and for extracting the CT values corresponding to the points in the segmented abdominal aorta region, and computing the added average CT values of the abdominal aorta region in the arterial phase and the delayed phase relative to the plain scan images.

A curve determining subunit 2033 is provided to obtain a curve of the average CT value of the abdominal aorta region varying with time by a regression analysis.

The curve of the CT value of the abdominal aorta varying with time is obtained by regression analysis, based on the average CT values of the abdominal aorta during the plain scan, the arterial phase and the delayed phase, as well as the time values.

A glomerular filtration rate determining subunit 2034 is provided to compute the glomerular filtration rates through a certain formula based on the above parameters and curve.

The characteristic data computing unit 203 may further include the following subunit:

a correcting subunit 2035, for correcting the computed glomerular filtration rates and obtaining corrected glomerular filtration rates, wherein the correction may be configured by one skilled in the art as required.

The part recognizing unit 202 may further include: a right and left kidney distinguishing subunit 2027, for determining the right and left kidneys in the kidney regions. The glomerular filtration rate determining subunit may be used to compute the glomerular filtration rates of the right and left kidneys respectively. Then the glomerular filtration rates of the right and the left kidney may be computed separately as required, thus overcoming the defect in the prior that the glomerular filtration rates of both the kidneys have to be computed simutaneously, and helping the physicians to assess the functions of the right and left kidneys respectively.

Figure 3:
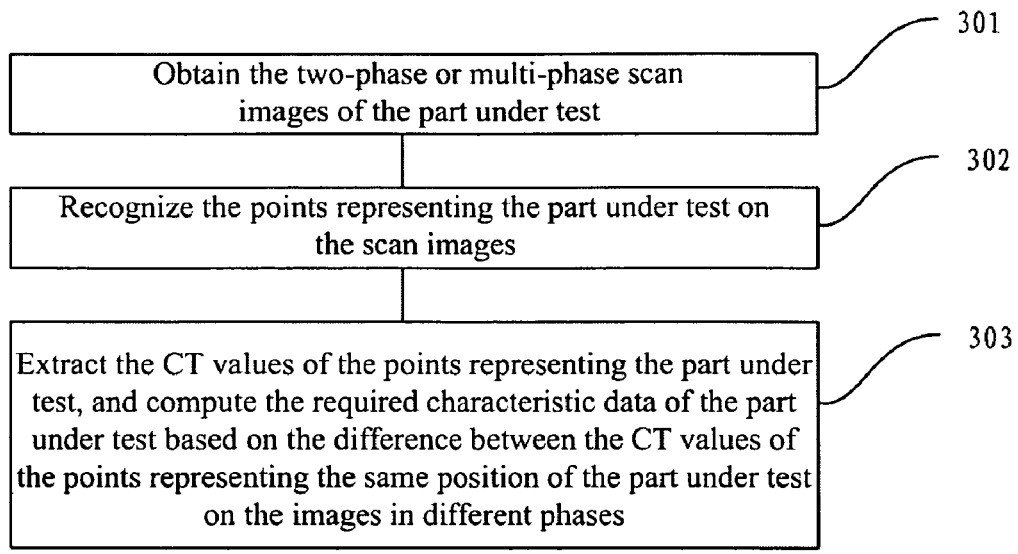
FIG. 3 shows a flow chart of a method for measuring abdominal CT images according to an embodiment of the present invention.

Referring to FIG. 3, there is shown a flow chart of a method for measuring abdominal CT images according to an embodiment of the present invention. The method includes:

in Step 301, the two-phase or multi-phase scan images of the part under test are obtained. The scan images including plain scan images and enhanced scan images;

in Step 302, the points representing the part under test on the scan images are recognized; and in Step 303, the CT values of the points representing the part under test are extracted, and the required characteristic data of the part under test are computed based on the difference between the CT values of the points representing a same position of the part under test on the images in different phases.

The method shown in FIG. 3 can be performed on the apparatus shown in FIG. 1, of which the related content has been described previously in detail, and it will be omitted here.

Figure 4:
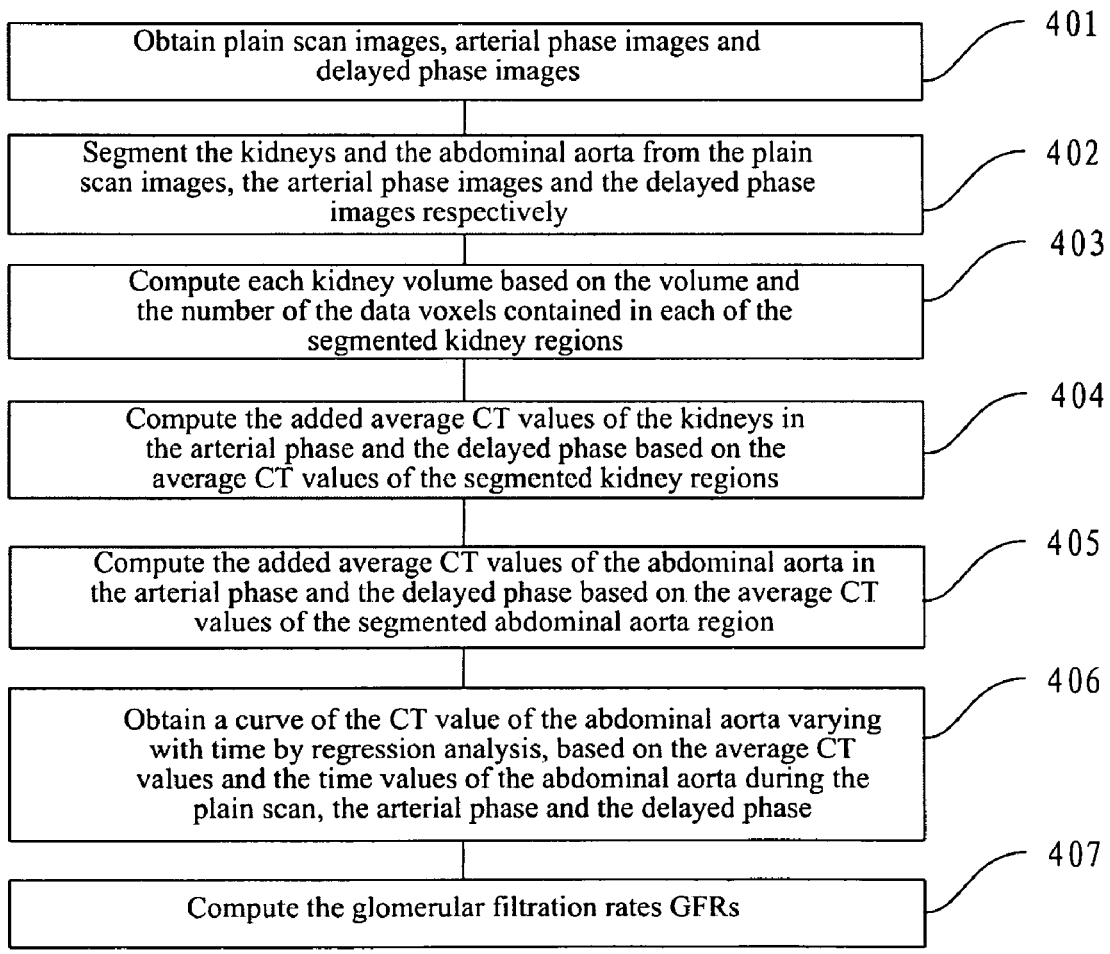
FIG. 4 is a flow chart of an image measuring method for glomerular filtration rate according to an embodiment of the present invention.

Referring to FIG. 4, there is shown a flow chart illustrating the steps of an image measuring method for glomerular filtration rate according to an embodiment of the present invention. FIG. 4 shows an application of the concept of the present invention to clinical medicine (the field of renal function estimation), for implementing the image measuring for glomerular filtration rate. And referring to FIG. 5, the information flow chart of the image measuring method for glomerular filtration rate is described herein in detail. It is noted that there is not a restriction on order for the steps for obtaining the required parameters in FIG. 4, so long as the required parameters may be obtained.

The evaluation of renal function is very important for the diagnosis of kidney diseases. The state-of-the-art laboratory methods are poor in sensitivity, and cannot provide the condition of unilateral renal function. The nuclear medical examinations cannot provide detailed anatomical information and need special apparatus. In the evaluation of renal function, Glomerular Filtration Rate (GFR) is an important index reflecting the filtration function of kidneys, by which the abnormal variation of the glomerular function may be predicted in an early time.

Currently, many methods for determining GFR may be employed clinically (for example, inulin clearance rate, isotope tag clearance rate, blood creatinine determination and endogenous creatinine clearance rate, etc.). However, there exist defects in all of these methods, such as low accuracy, multiple sampling on patients, radioactivity and no unified calibration standard, etc. Due to the linear relationship between the added CT value of the enhanced kidney and the concentration of contrast medium, GFR may be computed by the measurement of CT value.

Figure 5:
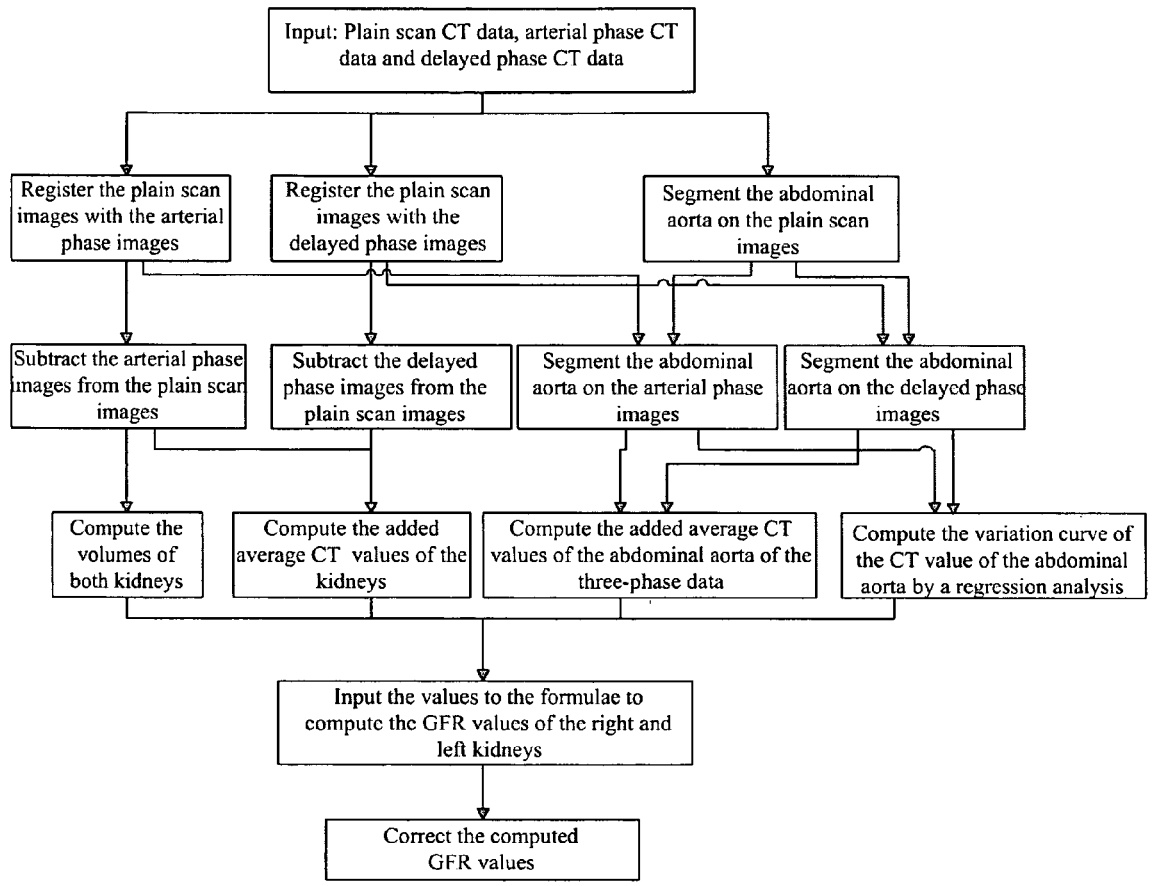
FIG. 5 is an information flow chart of the method as shown in FIG. 4.

The image measuring method for glomerular filtration rate of FIG. 4 and FIG. 5 is carried out based on the above principle, which method includes the following steps.

In Step 401, plain scan images, arterial phase images and delayed phase images are obtained.

The above three phase images may be obtained by CT scans. For example, the plain scan images are firstly obtained by a scan; the arterial phase scan begins after about 30 s since the injection of a contrast medium; and the parenchyma phase scan begins after about 100 s since the injection. It is noted there is no need in the embodiments of the present invention to determine which contrast medium is to be used clinically and how long after the injection of the contrast medium the arterial phase scan and the parenchyma phase scan will begin. Those may be determined by the operators themselves based on their experience or on the individual difference between the patients.

In Step 402, the kidney and the abdominal aorta are segmented from the plain scan images, the arterial phase images and the delayed phase images respectively.

In this step, the segmentation of the kidneys may be implemented by digital subtraction method, region growing method, watershed algorithm or ASM algorithm; and the segmentation of the abdominal aorta may be implemented by selecting a region through the digital subtraction method, the region growing method or manually.

Figure 6:
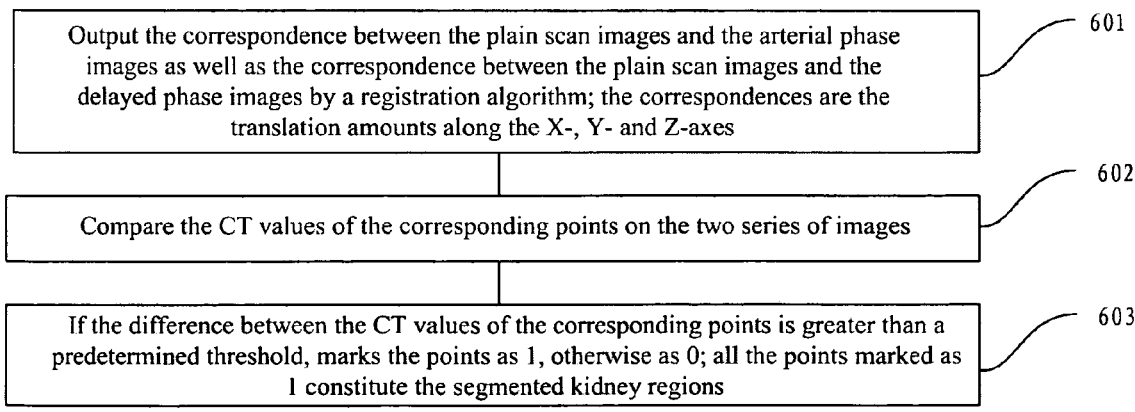
FIG. 6 is a flow chart of part recognization according to an embodiment of the present invention.

Referring to FIG. 6, in Step 402, the kidney may also be segmented by the following substeps.

In Substep 601, the correspondence between the plain scan images and the arterial phase images as well as the correspondence between the plain scan images and the delayed phase images are output by a registration algorithm.

In Substep 602, the CT values of the corresponding points on two series of images are compared; and In Substep 603, if the difference between the CT values of the corresponding points is greater than or equal to a predetermined threshold, each of the points are marked as 1, otherwise as 0; all the points marked as 1 constitute the segmented kidney region which may be displayed on the images to facilitate the viewing of related persons.

This step has been described in FIG. 2, so it will not be further illustrated here.

Though the abdominal aorta may also be segmented by the above method, but in a preferred embodiment of the present invention, the following method is put forward according to the characteristics of the abdominal aorta on the CT images. When the CT images of the whole abdominal aorta form, the distribution of CT values of the points in the abdominal aorta region on the images is comparatively uniform, so it is not necessary to determine all the points representing the abdominal aorta accurately. When a part of the points is determined, the average CT value of the abdominal aorta can be determined accurately. However, it is only needed for the evaluating of glomerular filtration rate, because no other characteristic data of abdominal aorta is needed during this measuring process. Furthermore, the average CT value of the abdominal aorta may be computed by using a certain region, a certain position, or a certain number of points selected by a user.

Preferably, region growing method is employed to segment the abdominal aorta, which includes the following steps: a point at the abdominal aorta on the plain scan images is selected as a seed point; a region growing is started to obtain a region of which the CT value is greater than a preset growing threshold, and the region is the segmented abdominal aorta on the plain scan images.

Next, the abdominal aorta will be segmented from the arterial phase images and the delayed phase images by the following step:

a region corresponding to the segmented abdominal aorta on the plain scan images is obtained in the arterial phase -images and the delayed phase images, based on the segmented abdominal aorta on the plain scan images and the correspondence between the plain scan images and the arterial phase images as well as the correspondence between the plain scan images and the delayed phase images output by a registration algorithm during the above segmentation of the kidneys.

Figure 7:
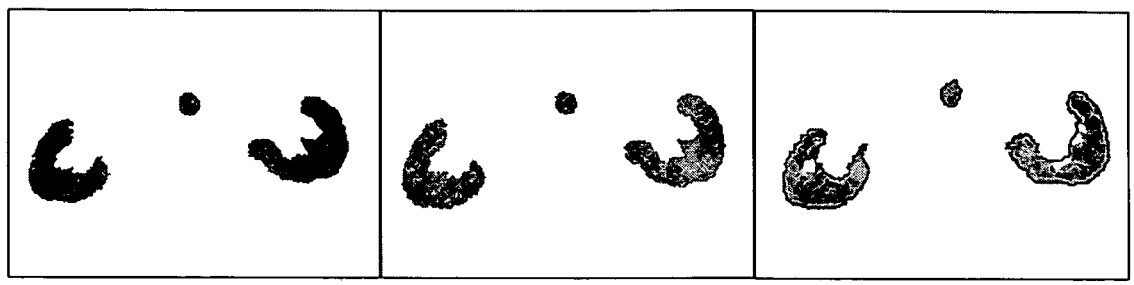
FIG. 7 is the result views of the part recognizzation displayed on images according to an embodiment of the present invention.

Referring to FIG. 7, there is shown the result views of the kidney segmentation and the abdominal aorta segmentation in the plain scan images, the arterial phase images and the delayed phase images, which are arranged form left to right. 701 is the contour of the abdominal aorta, and 703 and 702 are respectively the contours of the right and left kidneys in the images. In fact, all the corresponding points on the images contained in the stereoscopic kidneys or abdominal aorta may be recognized in the embodiments of the present invention.

In Step 403, each kidney volume is computed based on the volume and the number of the data voxels contained in each of the segmented kidney regions.

Taking plain scan data as an example, the side lengths of the data voxels are read out from the CT data (a file in Dicom format), as $X_{vox}$, $Y_{vox}$ and $Z_{vox}$ respectively. The points marked as 1 in Step 402 are counted, and the number of the voxels in the segmented regions of the right kidney and the left kidney are obtained as $N_L$, $N_R$ respectively. Thus the volumes of the right and left kidneys, $V_L$, $V_R$, are respectively:

$$V_L = N_L \cdot X_{vox} \cdot Y_{vox} \cdot Z_{vox},$$

$$V_R = N_R \cdot X_{vox} \cdot Y_{vox} \cdot Z_{vox}.$$

For example, the side lengths $X_{vox}$, $Y_{vox}$ and $Z_{vox}$ of the data voxels are 0.71 mm, 0.71 mm and 5 mm, respectively. The numbers of the data voxels of the segmented regions of the right and left kidneys, $N_L$, $N_R$, are 65463 and 61892 respectively. Then the volumes of the right and left kidneys, $V_L$ and $V_R$, are respectively:

$$V_L = N_L \cdot X_{vox} \cdot Y_{vox} \cdot Z_{vox} = 165 \text{ ml},$$

$$V_R = N_R \cdot X_{vox} \cdot Y_{vox} \cdot Z_{vox} = 156 \text{ ml}.$$

In Step 404, the added average CT values of the kidneys in the arterial phase and the delayed phase are computed based on the average CT values in the segmented kidney regions.

The average CT values of the right and left kidneys $I_{L0}$, $I_{R0}$, $I_{L1}$, $I_{R1}$, $I_{L2}$, $I_{R2}$ in the three series of data are computed. Then the added average CT values of the right and left kidneys in the arterial phase and the delayed phase, $\Delta I_{Lt1}$, $\Delta I_{Rt1}$, $\Delta I_{Lt2}$ and $\Delta I_{Rt2}$ are as follows:

$$\Delta I_{Lt1} = I_{L1} - I_{L0} = 110,$$

$$\Delta I_{Rt1} = I_{R1} - I_{R0} = 114,$$

$$\Delta I_{Lt2} = I_{L2} - I_{L0} = 95,$$

$$\Delta I_{Rt2} = I_{R2} - I_{R0} = 98.$$

In Step 405, the added average CT values of the abdominal aorta in the arterial phase and the delayed phase are computed based on the average CT values on the segmented abdominal aorta region.

The average CT values of the abdominal aorta $I_{A0}$, $I_{A1}$, $I_{A2}$ computed for the segmented abdominal aorta region in the three series of data are 20, 86 and 52 respectively. Then the added average CT values of the abdominal aorta $b(t_1)$, $b(t_2)$ in the arterial phase and the delayed phase are respectively:

$$b(t_1) = I_{A1} - I_{A0} = 86 - 20 = 66,$$

$$b(t_2) = I_{A2} - I_{A0} = 52 - 20 = 32.$$

Figure 8:
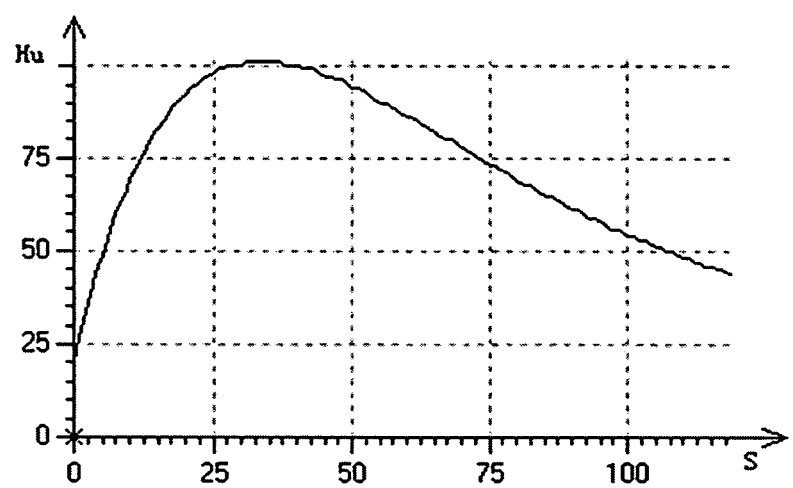
FIG. 8 shows a relation curve of the abdominal aorta CT value obtained by regression analysis vs. time according to an embodiment of the present invention.

In Step 406, the curve of the CT value of the abdominal aorta varying with time is obtained by regression analysis, based on the average CT values and time values of the abdominal aorta during the plain scan, the arterial phase and the delayed phase. Referring to FIG. 8, there is shown a curve of the result view obtained after Step 406. The X-coordinate represents time (s), and the Y-coordinate represents CT value (Hu). In general, other curves of the CT value of abdominal aorta varying with time are substantially similar to the curve shown in FIG. 8.

The method for obtaining the curve includes the following steps.

A t-I coordinate system of CT value vs time is set up; three points (0,0), $(t_1, b(t_1))$ and $(t_2, b(t_2))$ in the t-I coordinate system are obtained from the three series of data, wherein t1 and t2 are the time interval between the plain scan and the arterial phase scan as well as the time interval between the plain scan and the delayed phase scan. It is known that the variation curve of aorta CT value complies with the formula:

$$I(t) = A \cdot e^{-\frac{t}{B}} + C \cdot e^{-\frac{t}{D}}.$$

The aorta CT value variation curve may be obtained by regression analysis algorithm according to this formula and the three points in the t-I coordinate system.

For example, the three points (0,0), $(t_1, b(t_1))$ and $(t_2, b(t_2))$ maybe (0,0), (30,66) and (100,32); and the aorta CT value variation curve obtained by regression analysis algorithm is shown as in FIG. 8.

In Step 407, the glomerular filtration rate GFR is computed.

The GFR values of the right and left kidneys may be computed by the following formula (1) and formula (2) respectively in Step 407:

$$GFR'_L = \frac{V_L \cdot \Delta I_{Lt2} - \frac{b(t_2)}{b(t_1)} \cdot V_L \cdot \Delta I_{Lt1}}{\int_0^{t_2} b(t)dt - \frac{b(t_2)}{b(t_1)} \int_0^{t_1} b(t)dt}, \quad (1)$$

$$GFR'_R = \frac{V_R \cdot \Delta I_{Rt2} - \frac{b(t_2)}{b(t_1)} \cdot V_R \cdot \Delta I_{Rt1}}{\int_0^{t_2} b(t)dt - \frac{b(t_2)}{b(t_1)} \int_0^{t_1} b(t)dt}. \quad (2)$$

Wherein, $V_L$ and $V_R$ represent the volumes of the right and left kidneys, respectively;

$\Delta I_{Lt1}$, $\Delta I_{Rt1}$, $\Delta I_{Lt2}$ and $\Delta I_{Rt2}$ represent the added average CT values of the right and left kidneys during the arterial phase and the delayed phase;

t is the scan time after the injection of the contrast medium, and t1 is the arterial phase scan time, t2 is the parenchyma phase scan time;

$b(t_1)$ and $b(t_2)$ and represent the added average CT values of the abdominal aorta during the arterial phase and the delayed phase, respectively;

In general, the unit of the computed GFR is ml/min. The unit used may also be determined by the related persons and has no effect on the implementation of the present invention.

Preferably, the image measuring method for glomerular filtration rate may further includes: correcting the glomerular filtration rate by using the hematocrit level, and obtaining a corrected glomerular filtration rate, with a correction formula of:

$GFR = (1-hct) \cdot c_2,$ wherein hct is the hematocrit level, which may be obtained by clinical assays, or may be computed by the following formula:

$hct = 0.0083 b_{un} + 0.0244,$ wherein $b_{un}$ is the average CT value of the abdominal aorta on the plain scan images.

For example, the uncorrected GFR value (ml/min) of the left kidney is 94, and the uncorrected GFR value (ml/min) of the right kidney is 91; while the corrected GFR value (ml/min) of the left kidney is 52, and the corrected GFR value (ml/min) of the right kidney is 50.

However, other corrected or modified formulae for other purpose may be employed. In addition, less number of parameters than those used in formula (1) may be employed in the formula for computing the glomerular filtration rate GFR. The number of parameters used is not restricted in the present invention and may be selected by those skilled in the art as required. One of the key concepts of the present invention is characterized in that: kidney and abdominal aorta are segmented, and the parameters as required to compute the GFR are extracted based on the segmentation results. This technical solution may improve the precision while the efficiency is guaranteed; therefore the computation of the glomerular filtration rate GFR may be realized in easy and convenient ways, thus, suitable for clinical applications.

For obtaining the glomerular filtration rate GFR, the following method is usually employed to select parameters in the prior art.

Kidney volume: the kidney volume is determined by an operator according to his or her experiences; or a region may be approximately determined by the operator according to scanned images, for example, a region may be marked on the images by a curve, then the region may be measured by various ways, and thus the characteristic data of the part under test may be obtained.

The added average CT values of kidney and abdominal aorta: In general, some discrete points may be extracted on the approximately determinded region; the added average CT values of those discrete points may be computed to approximately obtain the added average CT values of the whole kidney and the abdominal aorta. In addition, due to the non-uniformity of the distribution of the CT values in the kidney, in order to obtain more accurate added average CT values, some operators extract some discrete points from each slice of the 3D CT data, and then compute the added average CT values of the selected discrete points and obtain the added average CT values of the whole kidney and the abdominal aorta.

Concentration curve of abdominal aorta contrast medium: Fine scans (for example, once per 2-3 s or the like) are performed on one slice of the above approximate region, and then connect the average CT values at these scan time points and obtain the required curve. But patients may suffer a larger amount of X-ray radiation.

After the above parameters are obtained, GFR values may be obtained by corresponding formulae.

It can be seen from the parameter obtaining process that in the prior art, the precision of obtained the GFR value is lower (some parameters must be estimated in order to increase the measuring speed), or the measuring speed and the efficiency are lower (considerable time is needed to obtain more accurate parameters in order to raise the precision).

The existing measuring solutions are acceptable for laboratory and theory studies that have low requirements on measuring time and measuring precision. However, those solutions are not suitable for clinical applications, because there exist great individual differences in clinical applications, more accurate measuring values are needed; and higher measuring speed are also needed, for the operators cannot bear a lengthy measuring time; moreover, the patients cannot suffer multiple or long X-ray scans due to their body condition. The above problems may be resolved by the image measuring method for glomerular filtration rate according to the embodiments of the present invention, which is easy to operate and is suitable for clinical application, and has a precision that meets the clinical requirements.

Figure 9:
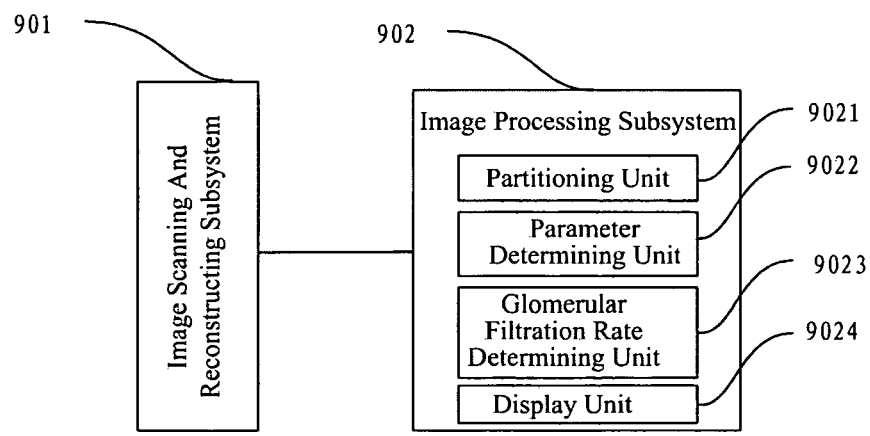
FIG. 9 shows a structure diagram of an image measuring system for glomerular filtration rate according to an embodiment of the present invention.

Refer to FIG. 9, there is shown a structure diagram of an image measuring system for glomerular filtration rate according to an embodiment of the present invention, which includes the following components.

An image scanning and reconstructing subsystem 901 is provided to scan and output plain scan images, arterial phase images and delayed phase images.

The image scanning and reconstructing subsystem may be implemented in various existing way. In general, the following parts are needed: a generator for generating X-rays, and an image reconstructing unit for detecting the X-rays transmitted from the samples due to the X-ray radiatation on the samples and for generating images. For this is well-known to those skilled in the art, so it will not be described in detail here.

An image-processing subsystem 902 is provided including:

a segmenting unit 9021, for segmenting kidneys and abdominal aorta in the plain scan images, the arterial phase images and the delayed phase images respectively;

a parameter determining unit 9022, for obtaining the volume and the number of data voxels contained in each of the kidney regions, computing each kidney volume, obtaining the average CT values of the kidney regions and the abdominal aorta region and computing the added average CT values of the kidneys and the abdominal aorta in the arterial phase and the delayed phase, and obtaining the average CT values and time values of the abdominal aorta during the arterial phase and the delayed phase and obtaining a curve of the average CT value of the abdominal aorta varying with time by regression analysis;

a glomerular filtration rate determining unit 9023, for computing the glomerular filtration rate based on the above parameters; and a display unit 9024, for displaying the glomerular filtration rate.

When used in clinical applications, the information displayed by the display unit may further include the segmented kidneys and abdominal aorta, and/or the curve of the CT value of the abdominal aorta varying with time.

For those not detailed in FIG. 9, reference may be made to the related parts of the specification.

The abdominal CT image measuring method and apparatus, and the image measuring system for glomerular filtration rate provided in the present invention have been described in detail according to the embodiments of the present invention. The description of the foregoing embodiments is intended to be illustrative, but not to limit the scope of the present invention. Many alternatives, modifications, and variations can be made by those skilled in the art, without departing from the basic principle of the present invention; any of those alternatives, modifications and variations shall fall into the protected scope of the present invention defined by the accompanied claims.

What is claimed is:

1. An abdominal CT image measuring apparatus, comprising:

an interface unit, for obtaining two-phase or multi-phase scan images of a part under test, wherein said scan images comprise plain scan images series and enhanced scan image series;

a part recognizing unit, for outputting a correspondence between the scan images in two different phases obtained by the interface unit by a registration algorithm, for comparing CT values of corresponding points on the scan images in two different phases, and for determining the corresponding points on the scan images in two different phases belong to the part under test when a difference between the CT values of said corresponding points is greater than or equal to a predetermined threshold; and a characteristic data computing unit, for extracting the CT values of said points representing the part under test, and computing required characteristic data of the part under test based on the difference between the CT values of the points representing a same position of the part under test on the images in different phases.

2. The abdominal CT image measuring apparatus according to claim 1, wherein said points belonging to the part under test together constitute said part under test and are displayed on the abdominal CT images.

3. The abdominal CT image measuring apparatus according to claim 1, wherein said plain scan images are abdominal CT plain scan images, said enhanced scan images comprise abdominal CT arterial phase images and abdominal CT delayed phase images, and said part under test includes kidneys and abdominal aorta; and said part recognizing unit is used for recognizing the points representing the kidneys and the abdominal aorta on the plain scan images, the arterial phase images and the delayed phase images, and for segmenting a kidney region and an abdominal aorta region.

4. The abdominal CT image measuring apparatus according to claim 3, wherein said characteristic data computing unit comprises:

a kidney volume determining subunit, for extracting the volume and the number of data voxels contained in each of said segmented kidney regions and computing each kidney volume;

an added average CT value determining subunit, for extracting the CT values corresponding to the points in said segmented kidney regions, computing the added average CT values of the kidney regions in the arterial phase and the delayed phase relative to the plain scan images, extracting the CT values corresponding to the points in said segmented abdominal aorta region, and computing the added average CT values of the abdominal aorta region in the arterial phase and the delayed phase relative to the plain scan images;

a curve determining subunit, for obtaining a curve of the average CT value of the abdominal aorta region varying with time by a regression analysis; and a glomerular filtration rate determining subunit, for computing the glomerular filtration rates based on the above parameters.

5. The abdominal CT image measuring apparatus according to claim 3, wherein said part recognizing unit comprises:

a selecting subunit, for selecting a point at the abdominal aorta on the plain scan images as a seed point; and a growing subunit, for starting a region growing from said seed point and obtaining a region of which the CT value is greater than a preset growth threshold, wherein said region is the segmented abdominal aorta on the plain scan images.

6. The abdominal CT image measuring apparatus according to claim 5, wherein said part recognizing unit further comprises:

an abdominal aorta region determining subunit, for obtaining, on the arterial phase images and the delayed phase images, a region corresponding to the segmented abdominal aorta on the plain scan images, based on said segmented abdominal aorta on the plain scan images and the correspondence between the plain scan images and the arterial phase images as well as the correspondence between the plain scan images and the delayed phase images output by the registration algorithm.

7. The abdominal CT image measuring apparatus according to claim 4, wherein said characteristic data computing unit further comprises:

a correcting subunit, for correcting the computed glomerular filtration rates.

8. The abdominal CT image measuring apparatus according to claim 4, wherein said part recognizing unit further comprises a right and left kidney distinguishing subunit, for determining the right and left kidneys in said kidney regions; and said glomerular filtration rate determining subunit is used for computing the glomerular filtration rates of the right and left kidneys respectively.

9. A method for measuring abdominal CT images, comprising:
an obtaining step, for obtaining two-phase or multi-phase scan images of a part under test, wherein said scan images comprise plain scan image series and enhanced scan image series;
a recognizing step, for outputting a correspondence between the scan images in two different phases by a registration algorithm, for comparing CT values of corresponding points on the scan images in the two different phases, and for determining the corresponding points on the scan images in the two different phases belong to the part under test when a difference between the CT values of said points is greater than or equal to a predetermined threshold; and
a computing step, for extracting the CT values of said points representing the part under test, and computing required characteristic data of the part under test based on the difference between the CT values of the points representing a same position of the part under test on the scan images in different phases.

10. The method for measuring abdominal CT images according to claim 9, wherein said points belonging to the part under test together constitute said part under test and are displayed on the abdominal CT images.

11. The method for measuring abdominal CT images according to claim 9, wherein
said scan images comprises abdominal CT plain scan images, arterial phase images and delayed phase images; and
points representing kidney and abdominal aorta on the plain scan images, the arterial phase images and the delayed phase images are recognized, and kidney regions and an abdominal aorta region are segmented.

12. The method for measuring abdominal CT images according to claim 11, wherein said computing step comprises:
extracting the volume and the number of data voxels contained in each of said segmented kidney regions, and computing each kidney volume;
extracting the CT values corresponding to the points in said segmented kidney regions, and computing the added average CT values of the kidney regions in the arterial phase and delayed phase relative to the plain scan images;
extracting the CT values corresponding to the points in said segmented abdominal aorta region, and computing the added average CT values of the abdominal aorta region in the arterial phase and the delayed phase relative to the plain scan images;
obtaining a curve of the average CT value of the abdominal aorta region varying with time by a regression analysis; and
computing the glomerular filtration rates based on the above parameters.

13. The method for measuring abdominal CT images according to claim 11, wherein the abdominal aorta is segmented on the plain scan images by the following steps:
selecting a point at the abdominal aorta on the plain scan images as a seed point; and
starting a region growing from said seed point and obtaining a region of which the CT value is greater than the preset growth threshold, wherein said region is the segmented abdominal aorta on the plain scan images.

14. The method for measuring abdominal CT images according to claim 13, wherein the abdominal aorta is segmented from the arterial phase images and the delayed phase images by the following step:
obtaining, on the arterial phase images and the delayed phase images, a region corresponding to the abdominal aorta segmented on the plain scan images, based on said segmented abdominal aorta on the plain scan images and the correspondence between the plain scan images and the arterial phase images as well as the correspondence between the plain scan images and the delayed phase images output by the registration algorithm.

15. The method for measuring abdominal CT images according to claim 12, further comprising:
correcting the computed glomerular filtration rates.

16. The method for measuring abdominal CT images according to claim 12, wherein
said recognizing step further comprises determining the right and left kidneys from said kidney regions; and
said computing step further comprises computing the glomerular filtration rates of the right and left kidneys respectively.

17. An image measuring system for glomerular filtration rate, comprising an image scanning and reconstructing subsystem and an image-processing subsystem, wherein
said image scanning and reconstructing subsystem is used for scanning and outputting plain scan images, arterial phase images and delayed phase images; and
said image-processing subsystem is used for image processing and characteristic data measuring, and comprises:
a segmenting unit, for segmenting kidney and abdominal aorta from the plain scan images, the arterial phase images and the delayed phase images respectively;
a parameter determining unit, for obtaining the volume and the number of data voxels contained in the segmented kidney regions and computing each kidney volume, obtaining the average CT values of said kidney regions and the segmented abdominal aorta region, computing the added average CT values of the kidneys and the abdominal aorta in the arterial phase and the delayed phase, and obtaining a curve of the average CT value of the abdominal aorta varying with time by a regression analysis;
a glomerular filtration rate determining unit, for computing the glomerular filtration rates based on the above parameters; and
a display unit, for displaying said glomerular filtration rates.

18. The image measuring system for glomerular filtration rate according to claim 17, wherein the information displayed on said display unit further comprises: the segmented kidney regions and abdominal aorta region, or the curve of the average CT value of said abdominal aorta varying with time.

* * * * *